April 9, 1963 J. WALLNER ET AL Plant Pat. 2,250
MAGNOLIA TREE
Filed Aug. 29, 1961 2 Sheets-Sheet 1
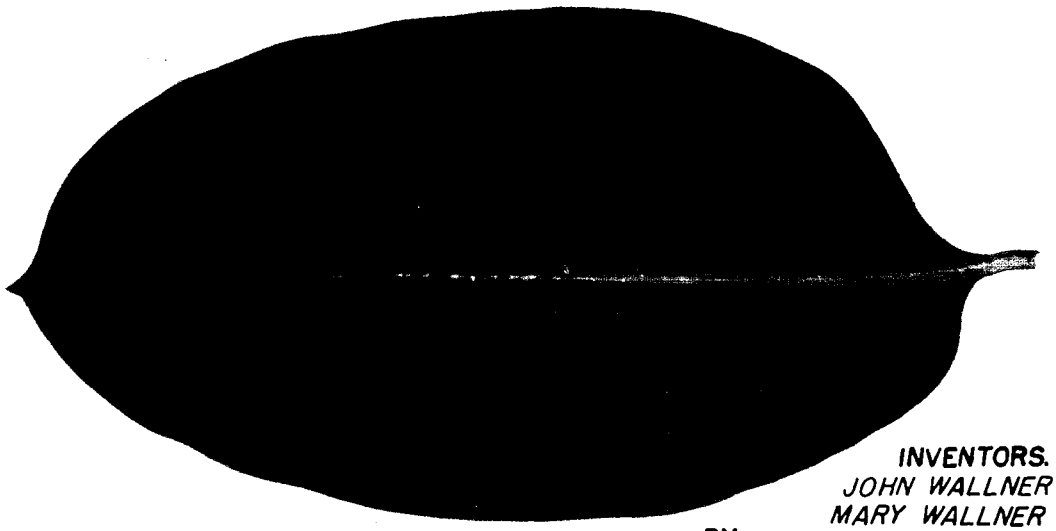
INVENTORS.
JOHN WALLNER
MARY WALLNER
BY J. F. Cuneo
ATTORNEY MAGNOLIA TREE
Filed Aug. 29, 1961 2 Sheets-Sheet 2
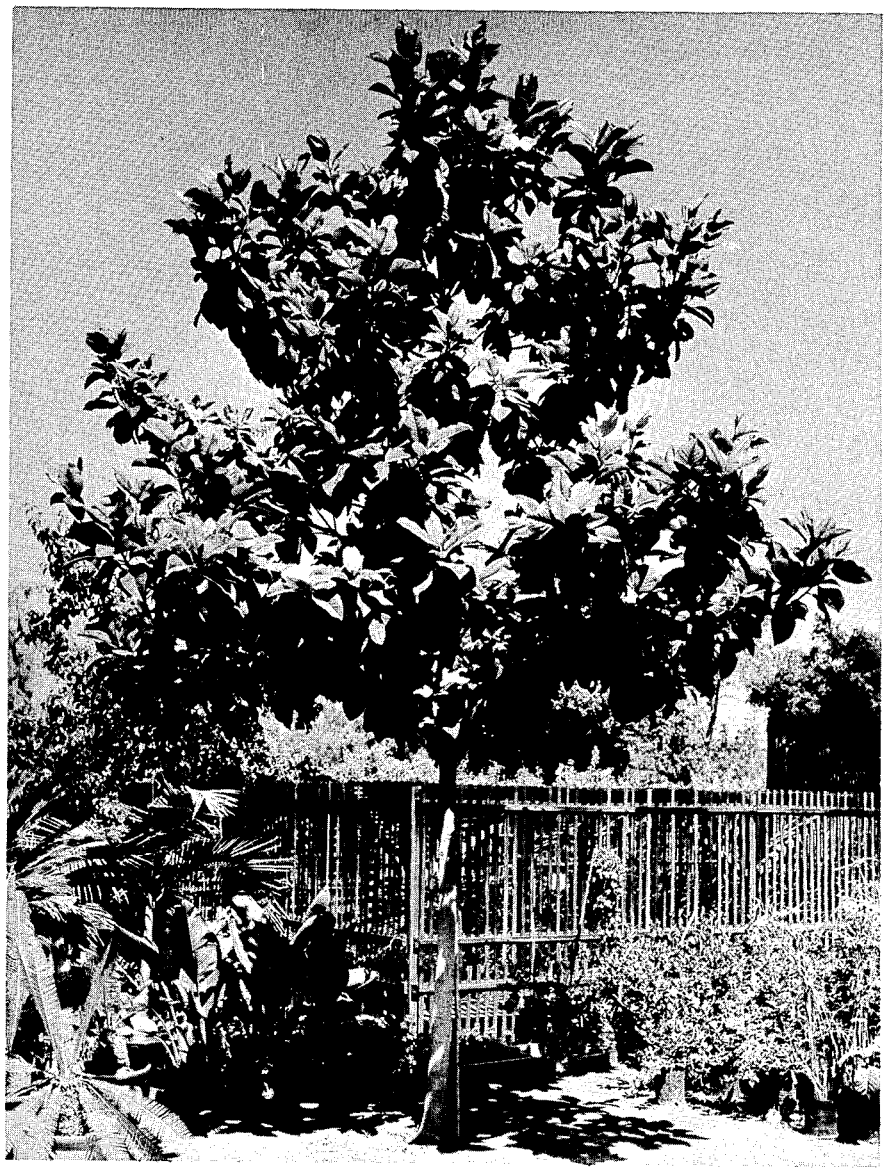
INVENTORS.
JOHN WALLNER
MARY WALLNER
BY J. F. Cuneo
ATTORNEY United States Patent Office Plant Pat. 2,250
Patented Apr. 9, 1963

2,250
MAGNOLIA TREE

John Wallner and Mary Wallner, Pasadena, Calif., assignors to Monrovia Nursery Company, Azusa, Calif., a corporation of California Filed Aug. 29, 1961, Ser. No. 134,789
1 Claim. (Cl. 47—60)

The present invention relates to a new and distinct variety of *Magnolia grandiflora* tree of the evergreen type.

We discovered this new variety on our cultivated property located at 1703 North Fair Oaks Avenue, in the city of Pasadena, county of Los Angeles, State of California, in June of 1951. The new variety originated as a so-called chance seedling of cultivated *Magnolia grandiflora*, an unpatented species, the pollen parent being unknown.

The new variety has been asexually reproduced by us at our property in Pasadena, California, primarily by grafting. Thousands of grafts of the new and distinct variety have been made since 1951, and in all instances the descendants have exhibited the distinguishing characteristics of the new variety, thereby establishing that the strain is true. The plant cannot be reproduced true from seed.

The new and distinct variety is characterized as to novelty by its symmetrical growth habit, by its dense and persistent foliage, and particularly by the very large leaves that are dark green and are substantially longer and wider than the leaves of other representatives of *Magnolia grandiflora*. An especially noticeable feature of this new variety is that the branches have an ascending growth habit in place of the usual horizontal habit.

The accompanying illustrations show in full color a leaf and a flower of the new variety. The black and white photograph shows the ascending growth habit of the branches, the symmetrical growth of the tree and the large heavy foliage. The leaves are a very dark green and the pigmentation employed for the leaves in the colored illustration is as close as could be produced with oils or water color.

A detailed description of the new and distinct variety of *Magnolia grandiflora* follows, and to faciltate identification of the important colors, the color terminology adopted by the British Horticultural Colour Charts, has been followed:

*The Tree*

Parentage: Chance seedling from *Magnolia grandiflora*, unpatented variety; pollen parent unknown.

Growth: The tree is vigorous, upright, and has a compact pyramidal crown with symmetrical branches. The ultimate size of the tree is unknown, but it is believed it should reach a height of at least fifty feet, if raised in a climate corresponding to that of the coastal region of southern California.

Branches:

*New growth.*—New branch growth is lightly pubescent.

*Mature growth.*—Mature branches exhibit a reddish brown bark that is smooth.

*Growth habit.*—Branches of the new species exhibit a pronounced ascending growth habit in place of horizontal.

Trunk: The trunk of the tree is provided with a smooth bark.

Foliage: The leaves are heavy, thick and glossy.

*Shape.*—The leaves are best described as oblong elliptic, with the ends abruptly acute. The base of the leaf is obtuse.

*Size.*—The full grown leaves are uniform in size and vary between five and one-half inches to six inches in width, and are between ten inches to ten and one-half inches in length.

*Arrangement.*—The leaves are alternate on the stems.

*Color.*—Upper side.—Ivy Green 0001061/1. Underside—Parsley Green 00962/2.

*Pubescence.*—The leaves have a light rusty pubescence on the underside.

*Petioles.*—Average three-quarters of an inch in length.

*Veins.*—The underside of each leaf has prominent veins extending from the midrib. The width of the midrib varies from three-sixteenths inches at its widest portion and reduces uniformly in thickness as it progresses toward the end of the leaf, vanishing completely at the end. The veins are lighter in color than the rest of the leaf.

*The Flower*

The plant blooms continuously from May to September, particularly during the months of June, July and August, when it puts out the greatest number of blooms. Some blooms will appear in September and October in southern California.

Form: Flowers are cup shaped as they open and become more bowl shaped as they mature. The flowers are similar to those of *Magnolia grandiflora*.

Petals: Petals vary between six and twelve.

Texture: The flowers are soft and leathery and have a velvety appearance.

Color: Creamy white.

Fragrance: Pleasant and mild.

Having described our invention, we claim:

The new and distinct variety of *Magnolia grandiflora* tree, substantially as shown and described, characterized particularly as to novelty by its unusually large and abundant foliage of uniform size having a very dark glossy green color on the upper side of the leaves with a lighter green underside, the prominent and large lighter green midrib and primary veins of the leaves and the vigorous, upright growth of the tree with symmetrical ascending branches to form a pyramidal crown.

No references cited.